United States Patent [19]

Patience et al.

[11] 4,219,024
[45] Aug. 26, 1980

[54] ABSORBENT ARTICLE

[75] Inventors: Donald Patience, Barrington; Hamzeh Karami, Crystal Lake, both of Ill.

[73] Assignee: Colgate-Palmolive Company, New York, N.Y.

[21] Appl. No.: 944,460

[22] Filed: Sep. 21, 1978

Related U.S. Application Data

[63] Continuation of Ser. No. 715,784, Aug. 19, 1978, abandoned.

[51] Int. Cl.³ ............................................. A61F 13/16
[52] U.S. Cl. ................................................... 128/287
[58] Field of Search ............... 128/284, 287, 290, 296; 428/283, 288, 290

[56] References Cited

U.S. PATENT DOCUMENTS

| | | | |
|---|---|---|---|
| 2,931,749 | 4/1960 | Kine et al. | 128/296 |
| 2,968,304 | 1/1961 | De Woskin | 128/290 R |
| 3,670,731 | 6/1972 | Harmon | 128/287 |
| 3,753,826 | 8/1973 | Plummer | 128/290 R |
| 3,804,092 | 4/1974 | Tunc | 128/284 |
| 3,828,783 | 8/1974 | Kennette et al. | 128/284 |
| 3,955,577 | 5/1976 | Gellert et al. | 128/290 R |
| 3,965,904 | 6/1976 | Mesek et al. | 128/284 |
| 3,976,074 | 8/1976 | Fitzgerald et al. | 128/284 |
| 4,104,062 | 7/1978 | Aberson et al. | 128/284 |

FOREIGN PATENT DOCUMENTS 828682  11/1975  Belgium ................................. 128/284

Primary Examiner—C. Fred Rosenbaum
Attorney, Agent, or Firm—Powell L. Sprunger

[57] ABSTRACT

An absorbent article for placement against a wearer to capture body fluids comprising, an absorbent pad comprising a mass of fibers, and particles of plastic material fused to fibers in the pad to increase the integrity and resiliency of the fibrous mass. The article has sheet means covering a front and back surface of the pad.

9 Claims, 6 Drawing Figures

U.S. Patent  Aug. 26, 1980  4,219,024
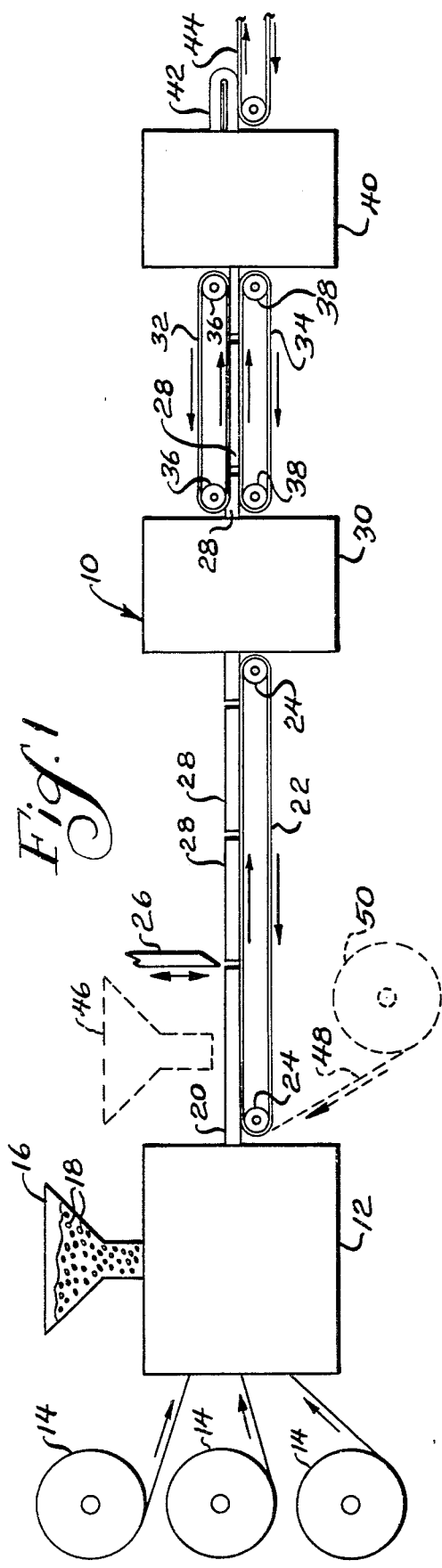

ABSORBENT ARTICLE

This is a continuation of application Ser. No. 715,784 filed Aug. 19, 1976 and now abandoned.

BACKGROUND OF THE INVENTION

The present invention relates to absorbent articles.

A various assortment of absorbent articles of the disposable type, such as diapers and sanitary pads, have been proposed which are discarded after a single use. Several factors are of importance in determining whether such articles will be acceptable to the consumer. The articles should rapidly receive and dissipate body fluids without a significant amount of backwetting to the wearer's skin, and should be available to the consumer at a relatively low cost, since they are not reused.

Much of the cost and deficienceis in prior articles may be attributed to the structure of and the materials used in the articles. In the case of disposable diapers, structures are often provided having an absorbent pad, a fluid impervious backing sheet covering a back surface of the pad, and a fluid pervious top sheet covering a front surface of the pad. Particularly in the case where the absorbent pads are made of a mass of fibers, such as comminuted wood pulp known in the art as fluff, an absorbent wadding sheet is often placed over the front surface of the pad to prevent balling and maintain structural integrity of the pad during use. In addition to adding to the cost of the diapers, such top wadding sheets impair the function of the diaper in a number of respects. The wadding sheets impede the rapdity of fluid passage from the top sheet into the pad, and retain fluid adjacent the front surface of the diaper, thus increasng the amount of backwetting from the diaper to the infant. The wadding sheet also adds stiffness to the diaper, thus decreasing the amount of comfort the diaper provides for the infant. In addition to lacking structural integrity, the fibers in the fluff pads collapse when wetted and placed under loads, thus decreasing the absorbent capacity of the pads.

As indicated above, many of the absorbent pads are currently made from wood fluff which is normally formed by fiberizing or comminuting pulp board. The pulp board itself is normally formed from trees through a pulping process. The pulping processes may be categorized as chemical, semichemical, mechanical, and thermomechanical. All of the wood fluff used in absorbent articles sold in the United States known to the applicant has been exclusively formed from a chemically produced pulp. For a given species of wood, the chemical pulping process produces a pulp having fibers with a longer length than the fibers produced by the other pulping processes, particularly the mechanical pulping process. Accordingly, the industry has sought chemically produced pulp for use in disposable pads since the long fibers enhance the structural integrity and loft of the pad.

In spite that the chemical pulp results in a pad with desirable characteristics, a number of disadvantages are inherent in the use of such pulp. First, the chemical pulping process is relatively inefficient in that the yield of pulp to the amount of wood used in pulping is in the range of 40 to 55%, whereas the yield of the mechanical and thermomechanical pulping processes is as high as 90-95%. The disparity in yields between the processes is due to the removal of lignin, cellulose, and hemicellulose from the wood during digestion in the chamical procedure. Accordingly, chemically produced pulps are significantly higher in cost than mechanical and thermomechanical pulps, necessarily resulting in a more costly item to the consumer. Also, the vital raw materials are not used to the desired extent in chemical pulps, thus detracting from our natural resources.

Second, environmental considerations favor the use of pulps which are not produced by the chemical process. In the chemical sulfite process, it is relatively difficult to reclaim the cooking chemicals used during pulping. Hence, the manufacturer must dispose of the chemicals, and it is believed that more than one sulfite processing plant has been closed due to contamination of water by the chemicals, which the Environmental Protection Agency considers dangerous. Although it is less difficult to reclaim the chemicals used in chemical kraft pulping, this process is characterized by the emission of gases containing malodorous substances, such as mercaptans and organic sulfides, and is also repugnant to the community at large.

Third, the energy required to fiberize pulp board solely of the chemical type is greater than that necessary for a pulp board containing mechanical or thermomechanical produced pulp. This follows since lignin of the fibers is removed during chemical pulping, thus increasing hydrogen bonding between dry fibers of the chemical pulp.

Finally, it is preferred to obtain an absorbent pad which overcomes the above objections, and yet has improved structural integrity and resiliency.

SUMMARY OF THE INVENTION

A principal feature of the present invention is the provision of an absorbent article of improved construction and reduced cost.

The article of the present invention comprises, an absorbent pad comprising a mass of fibers, and particles of plastic material fused to fibers in the pad. The article has sheet means covering a front and back surface of the pad.

A feature of the present invention is that the plastic material increases the structural integrity of the fibrous mass.

Thus, a feature of the present invention is that the article minimizes the possibility of breaking up and balling of the pad during use.

Another feature of the invention is that the plastic material eliminates the necessity for top and bottom wadding sheets for the pad.

Yet another feature of the invention is that the article permits rapid passage of fluid from the top sheet to the pad due to elimination of the top wadding sheet.

Another feature of the invention is that the article reduces back wetting from the pad due to elimination of the top wadding sheet.

A further feature of the invention is that the article is more pliable and has a better hand due to elimination of the top wadding sheet.

Thus, another feature of the invention is that the article of the present invention is more comfortable to the skin of the user.

A feature of the present invention is that a mass of shorter fibers, such as fluffs formed from mechanical, thermomechanical, or semichemically produced pulps may be used in the pad while the plastic material maintains sufficient structural integrity of the pad.

Another feature of the invention is the elimination of the top and back wadding sheets and the use of fluffs having shorter fibers reduces the cost of the absorbent article.

Still another feature of the invention is that the plastic material increases the resiliency of the pad during use. Thus, another feature of the invention is that the pad minimizes collapsing of fibers when the pad is wetted and placed under loads during use.

Further features will become more fully apparent in the following description of the embodiments of this invention and from the appended claims.

DESCRIPTION OF THE DRAWINGS

In the drawings:

FIG. 1 is a diagrammatic view illustrating an apparatus for making an absorbent article according to a method of the present invention;

FIG. 2 is a fragmentary front plan view illustrating an article in the form of a disposable diaper of the present invention;

FIG. 3 is a fragmentary sectional view of the diaper of FIG. 2;

FIG. 4 is a fragmentary sectional view of another embodiment of an article of the present invention;

FIG. 5 is a fragmentary sectional view of another embodiment of the article of the present invention; and FIG. 6 is a fragmentary sectional view of another embodiment of the article of the present invention.

DESCRIPTION OF THE PREFERRED EMBODIMENTS

Although, for convenience, the absorbent article of the present invention will be described as a disposable diaper, it will be understood that the description is applicable to other suitable absorbent articles. For example, other illustrative articles which may be constructed according to the present invention are sanitary pads, maternity napkins, and wound dressings.

Referring now to FIG. 1, there is shown an apparatus, generally designated 10, for making an absorbent article, such as a disposable diaper, according to a method of the present invention. The apparatus 10 has a first section 12 which receives pulp board from a plurality of feed rolls 14, and fiberizes the pulp board into a mass of fibers termed by the art as comminuted wood pulp or wood fluff. The types of wood pulp utilized in the feed rolls 14, or fed into the first section 12 by other suitable means, will be described in greater detail below. The first section 12 also receives a supply 16 of heat-sensitive plastic particles 18, and mixes the particles with fibers in the wood fluff. The particles of plastic material may be in any suitable form, such as powder, fibers, flakes, spheres, or shredded material, and may be of a thermoplastic material such as polyethylene, polypropylene, and Vinyon, a trademark of Union Carbide Corp., Charleston, West Virginia, or particles of a thermosetting plastic which may have a melting temperature less than the temperature which would otherwise damage the fluff.

As shown, the first section 12 forms the mixture of fluff and plastic particles into a web 20, and passes the web 20 onto an endless belt 22 which is supported and driven by a pair of rollers 24 in a direction such that the web 20 is carried from the first section 12. The web 20 may be cut into lengths by suitable means, such as a reciprocating knife 26, in order to define pad sections 28.

The pad sections 28 pass from the belt 22 into a second section 30 where the pads are heated in order to fuse the plastic particles to fibers in the pad. The second section may comprise an oven, a hot air applicator, or other suitable heating device. After the plastic materials have been melted in the heating section 30, the pad sections pass between upper and lower endless belts 32 and 34, respectively, which are respectively supported and driven by associated pairs of rollers 36 and 38. The belts 32 and 34 are driven in a direction such that the pad sections 28 are carried between the belts and are compressed by the belts while the plastic particles are still hot and are being fused to the fibers in the pad sections. In this manner, the plastic particles are pressed into the fibers and are fused to the fibers by compression of the pad sections. However, it is noted at this point, that the pad sections may be heated and compressed simultaneously by suitable means, such as by heated rolls. Alternatively, the pad sections need not be compressed if the sections are heated to a sufficient temperature or the relative percentage of the plastic materials to the fibrous mass is sufficiently large.

After compression, the pad sections 28 pass from the belts 32 and 34 into a third section 40 where final steps in the formation of the absorbent article take place. For example, in the case of a disposable diaper, a backing sheet of fluid impervious material may be placed against a back surface of the pad section, a fluid pervious top sheet may be placed against the front surface of the pad section, the top and backing sheets may be secured together, and the article or diaper is folded into the desired configuration, after which the diaper 42 passes from the third section 40 onto a belt 44 which carries the diapers to suitable apparatus for packaging the diapers.

In an alternative form, the thermoplastic particles may be placed against a surface of the web 20 or pad sections 28 by a supply 46 of plastic material. The thermoplastic or thermosetting plastic material may be spread in solid form on the pad sections, or the plastic material may be placed or sprayed in liquid form on the pad sections to form the particles, in which case further heating by the section 30 is not required. It will also be understood that the plastic materials may be placed against either of the outer surfaces of the pad section, or may be placed against both outer surfaces by inverting the pad or in another suitable manner. If desired, a carrier web 48 of tissue, such as a wadding sheet, may be unwound from a roll 50, and may be placed against the lower surface of the web 20, as shown, in order to facilitate movement of the web 20 prior to heating, particularly in the case where the plastic material is placed against the opposed surface by the supply 46.

According to a method of the present invention, the pad is made by forming a fibrous mass, positioning particles of heat-sensitive plastic material in the mass, and heating the mass to fuse the plastic particles to fibers in the mass. The fibrous mass may be compressed either during or after the heating step, and the plastic particles may be mixed with the fibers in the mass, or may be placed against an outer surface of the mass. Alternatively, the plastic material may be placed or sprayed on the pad sections in liquid form, after which the plastic material is permitted to harden and fuse particles of plastic material to fibers in the fibrous mass.

An absorbent article in the form of a disposable diaper is illustrated in FIGS. 2 and 3 in which different reference numerals will be utilized for purpose of clarity. The article or diaper generally designated 60 has an absorbent pad assembly 62 having a backing sheet 64 of fluid impervious material, such as polyethylene, defining a back surface 66 of the pad assembly 62, a fluid pervious top or cover sheet 68, such as a nonwoven material, defining a front surface 70 of the pad assembly 62, and an absorbent pad 72 located intermediate the backing sheet 64 and cover sheet 68. The pad assembly 62 has a pair of side edges 74, and end edges 76 connecting the side edges 74. The absorbent pad 72 has a front surface 78, a back surface 80, a pair of side edges 82, and end edges 84 connecting the side edges 82. In a preferred form, as shown, the side edges 82 of the pad 72 are located adjacent the side edges 74 of the pad assembly 62, and the backing sheet 64 has lateral side margins 86 folded over and secured to the front of the pad assembly and covering lateral side margins of the absorbent pad 72. The diaper 60 may have suitable tape fasteners 88 for use in securing the diaper about an infant.

As previously discussed, the absorbent pad 72 is made from a mass of fibers 90, and has particles 92 of heat-sensitive plastic material fused to the fibers 90 in the fibrous mass of the absorbent pad 72. In the embodiment shown, the plastic particles 92 extend substantially throughout the pad, and are dispersed between the side and end edges 82 and 84, respectively, of the pad 72, and between the opposed front and back surfaces 78 and 80, respectively, of the pad 72. As shown, the particles 92 are spaced throughout the pad in order to permit passage of fluid into the pad.

The fused plastic particles hold the pad fibers together and maintain the structural integrity of the pad without the necessity of top and back wadding sheets, and may be used with the same results to maintain structural integrity of fluffs formed from pulps other than chemical pulp. Accordingly, the cost of the pad 72 and diaper is reduced, since the top and back wadding sheets have been eliminated, and the non-chemical fluffs may be obtained at a significantly reduced cost. In addition, elimination of the top wadding sheet permits a more rapid passage of fluid from the top sheet into the pad, and reduces back wetting from the pad which is normally caused by the presence of the top wadding sheet. Further, the article is pliable and has a better hand due to elimination of the top wadding sheet, thus providing additional comfort to the skin of the wearer. In addition to adding structural integrity to the pad 72, the fused plastic particles 92 also increase the resiliency of the pad when wetted and placed under loads during use. In the past, the fibers in the usual chemical fluff collapse when wetted and placed under loads, thus reducing the interfiber spacings of the fluff and the absorbent capacity of the pad. In contrast, the fused particles 92 provide the pads 72 with resiliency, and increase the bulk and absorbent capacity during use.

As indicated above, the fused plastic particles 92 may be used to maintain the structural integrity of the pad even when formed from a non-chemical fluff having relatively short fibers. As will be discussed below, the pad 72 may be formed from a single type of such lower cost pulps, or the fibers from various pulps may be mixed into the pad.

As a background, the various pulping processes are discussed as follows. Pulping itself may be defined for the present purposes as a procedure for rupturing the fibers of wood. The resulting pulp may be used for making paper or in this case absorbent pads. The separated fibers of the pulp are normally formed into pulp board which may be wound into the feed rolls for convenience of handling during shipment and by the user. As discussed above, the rolls are fiberized or comminuted by the user to form the loosely formed fibrous mass which is cut into lengths as absorbent pads for the disposable articles.

Wood itself is primarily composed of cellulose, hemicellulose, and lignin. Lignin is an amorphous polymer of relatively high molecular weight that serves to hold the fibers of wood together. Cellulose is highly hydrophilic, while lignin has a significantly reduced affinity for liquid than cellulose and is relatively hydrophobic. Since pulping is concerned with rupturing the bonds between the wood fibers, the middle lamella between the fibers, which is composed mostly of lignin, must be ruptured during the procedure.

Wood logs are transported to the processor, after which bark from the logs may be removed. Generally, the logs are ground into chips, and the chips are used in the pulping procedure to separate fibers in the chips. The fibers are then washed to produce the unbleached pulp, after which the pulp may be bleached to a lighter color pulp. The process differs primarily in the manner the wood is pulped.

The pulping procedures may be categorized as mechanical, chemical, semichemical and thermomechanical. In mechanical pulping, the logs themselves may be ground by a roughened stone to grind fibers out of the wood. Alternatively, wood chips may be shredded or ground between metal shearing discs in a machine called a refiner. The mechanical pulps produced in this manner are characterized by relatively short fibers due to damage of the fibers during the procedure. Such groundwood processes are relatively efficient in that approximately 95% of the dry weight of the wood is converted into pulp, since materials, such as lignin, are not specially removed from the pulp.

In chemical pulping, the wood chips are cooked in a vessel or digester with chemical reagents to separate the fibers, termed a digesting procedure. During digesting, the pulping reagents degrade and dissolve the lignin to break the bond between the fibers in order that they may be separated. However, the reagents also degrade some of the cellulose and hemicellulose, and the loss of these materials, including lignin, accounts for the relative inefficiency of chemical pulping. Thus, the yield from chemical pulping may range from 40 to 50% of the weight of the wood, with a maximum yield of 55%. Accordingly, chemically produced pulps are significantly higher in cost than mechanical and thermomechanical pulps, the yield of the latter also believed to approach 95%, not to mention the loss of valuable materials during chemical pulping.

The chemically produced pulp is characterized by relatively long fibers which are mostly completely separated. As noted above, the lignin is removed, and the hydrophilic fibers thus produced are susceptible to increased wetting.

The two most common chemical procedures are the sulfite and kraft processes. In the sulfite procedure, an acidic mixture is used as the reagent which is relatively difficult to reclaim, thus posing a risk to the environment when disposed by the processor. In the kraft or sulfate process, the chips are cooked in a solution of sodium hydroxide, sodium carbonate and sodium sulfide. This process results in the emission of gases containing malodorous substances, and is also repugnant to the environment.

In the semichemical process, such as the neutral-sulfite process, the wood chips or logs are softened with a chemical, after which the wood is fiberized mechanically, frequently in disc refiners. The yield of the semichemical process is also higher than that of the chemical process.

Finally, in the thermomechanical procedure, wood chips are steamed at an elevated temperature and pressure to soften the lignin. Thus, the binding force between the fibers is greatly lessened through application of heat to permit separation of the fibers. The fibers may be separated by a refiner under pressure or pressure changes.

For convenience, the fibrous mass formed from a mechanically produced pulp will be termed a mechanical fluff, the fibrous mass formed from a thermomechanically produced pulp will be termed a thermomechanical fluff, the fibrous mass formed from a semichemically produced pulp will be termed a semichemical fluff, while the fibrous mass formed from a chemically produced pulp will be termed a chemical fluff. The average fiber length of the mechanical fluff is less than that of the thermomechanical fluff, the average fiber length of the thermomechanical fluff is less than that of the semichemical fluff, while the average fiber length of the semichemical fluff is less than that of the chemical fluff. Thus, under normal conditions the structural integrity and loft of the chemical fluff is greater than that of the other fluffs and accounts for the widespread use of chemical fluff. However, relative chemical fluffs, the fibers in the mechanical, thermomechanical, and semichemical fluffs contain a greater portion of their natural lignin, and the wet resilience of the fibers in the non-chemical fluffs is greater than that of the chemical fluff, thus providing the non-chemical fluffs with greater resiliency and fluid holding capacity when wetted and placed under loads.

In accordance with the present invention, the mechanical, thermomechanical, and semichemical fluffs may be used in the pad 72 with the fused plastic particles 92 providing the desired structural integrity of the pad, in spite that the fibers of the non-chemical fluffs have an average fiber length less than that of the usual chemical fluff. The pad may be made solely of mechanical fluff, thermomechanical fluff, or semichemical fluff, or may comprise a mixture of the non-chemical fluffs, a mixture of the non-chemical fluffs and a chemical fluff, or, if desired, solely from the more costly chemical fluff. Accordingly, due to higher pulp yields, the mechanical, thermomechanical, and semichemical fluffs are less costly than the usual chemical fluff, and to the extent that the mechanical, thermomechanical, or semichemical fluffs are used in the pad, the cost of the pad and diaper is reduced.

Another embodiment of the article or diaper 60 of the present invention is illustrated in FIG. 4, in which like reference numerals designate like parts. In this embodiment, the plastic particles 92 are placed on the front surface 78 of the pad 72, and are fused to the pad at this location. Accordingly, the particles 92 maintain the structural integrity of the pad adjacent the front surface in a manner as previously described. If desired, a back wadding sheet 94 may be placed against the back surface 80 of the pad 72.

Another embodiment of the invention is illustrated in FIG. 5, in which like reference numerals designate like parts. In this embodiment, the particles 92 of plastic material are placed on the back surface 80 of the pad 72 and are fused into place adjacent the lower part of the pad. Thus, the fused particles 92 maintain the structural integrity of the lower portion of the pad. If desired, the pad 72 may have a top wadding sheet 96 covering the front surface 78 of the pad 72.

Another embodiment of the present invention is illustrated in FIG. 6, in which like reference numerals designate like parts. In this embodiment, the particles 92 of plastic material are placed on both the front and back surfaces 78 and 80, respectively, of the absorbent pad 72. The particles 92 are fused to the pad fibers in a manner as previously described, and maintain the structural integrity of the front and back portions of the absorbent pad 72.

The foregoing detailed description is given for clearness of understanding only, and no unnecessary limitations should be understood therefrom, as modifications will be obvious to those skilled in the art.

We claim:

1. An absorbent article for placement against a wearer to capture body fluids, comprising: an absorbent pad comprising a mass of fibers including fibers formed from at least one of a thermomechanically, mechanically, or semichemically produced pulp, and particles of a heat-sensitive plastic material fused to fibers in the pad to increase the integrity and resiliency of the fibrous mass, and sheet means covering a front and back surface of the pad, said plastic particles being only located adjacent the front surface of the pad.

2. The article of claim 1 wherein the plastic particles comprise a powder.

3. The article of claim 1 wherein the plastic particles comprise fibers.

4. The article of claim 1 wherein said mass includes fibers formed from a chemically produced pulp.

5. The article of claim 1 wherein said article comprises a disposable diaper.

6. The article of claim 5 wherein said sheet means comprises, a fluid pervious top sheet covering at least a portion of the front surface of the pad, and a backing sheet of fluid impervious material covering at least a portion of the back surface of the pad.

7. The article of claim 1 wherein the plastic particles comprise a thermoplastic material.

8. The article of claim 1 wherein the plastic particles comprise a thermosetting material.

9. An absorbent article for placement against a wearer to capture body fluids, comprising: an absorbent pad comprising a mass of fibers including fibers formed from at least one of a thermomechanically, mechanically, or semichemically produced pulp, and particles of a heat-sensitive plastic material fused to fibers in the pad to increase the integrity and resiliency of the fibrous mass, and sheet means covering a front and back surface of the pad, said plastic particles being only located adjacent the back surface of the pad.

* * * * *